(12) United States Patent
Han et al.

(10) Patent No.: US 9,726,579 B2
(45) Date of Patent: Aug. 8, 2017

(54) SYSTEM AND METHOD OF CONDUCTING PARTICLE MONITORING USING LOW COST PARTICLE SENSORS

(71) Applicant: TSI, Incorporated, St. Paul, MN (US)

(72) Inventors: Hee-Siew Han, Maple Grove, MN (US); James E. Farnsworth, Shoreview, MN (US); Robert Caldow, Roseville, MN (US)

(73) Assignee: TSI, Incorporated, St. Paul, MN (US)

( * ) Notice: Subject to any disclaimer, the term of this patent is extended or adjusted under 35 U.S.C. 154(b) by 32 days.

(21) Appl. No.: 14/586,122

(22) Filed: Dec. 30, 2014

(65) Prior Publication Data

US 2016/0153884 A1 Jun. 2, 2016

Related U.S. Application Data

(60) Provisional application No. 62/086,414, filed on Dec. 2, 2014.

(51) Int. Cl.
*G01N 15/02* (2006.01)
*G01N 1/22* (2006.01)
*G01N 15/06* (2006.01)

(52) U.S. Cl.
CPC ........... *G01N 1/2205* (2013.01); *G01N 15/06* (2013.01); *G01N 1/2273* (2013.01); *G01N 2001/2223* (2013.01); *G01N 2015/0693* (2013.01)

(58) Field of Classification Search
None
See application file for complete search history.

(56) References Cited

U.S. PATENT DOCUMENTS

| | | | |
|---|---|---|---|
| 3,770,351 A | 11/1973 | Wyatt | |
| 4,804,853 A | 2/1989 | Borden et al. | |
| 5,001,463 A * | 3/1991 | Hamburger | G01N 1/2205 |
| | | | 340/627 |
| 5,084,614 A | 1/1992 | Berkner | |
| 5,085,500 A | 2/1992 | Blesener | |
| 5,121,988 A | 6/1992 | Blesener et al. | |
| 5,926,098 A * | 7/1999 | Wiemeyer | G08B 17/10 |
| | | | 250/573 |
| 6,831,289 B1 | 12/2004 | Preikszas et al. | |
| 7,038,189 B2 | 5/2006 | Kawai | |
| 7,111,496 B1 | 9/2006 | Lilienfeld et al. | |
| 7,932,490 B2 | 4/2011 | Wang et al. | |
| 8,009,290 B2 | 8/2011 | Unger | |

(Continued)

*Primary Examiner* — Robert R Raevis
(74) *Attorney, Agent, or Firm* — Kagan Binder, PLLC

(57) ABSTRACT

There is disclosed a field calibratable particle sensor solution in a low-cost, very compact form factor. This makes a low-cost sensor more accurate for low-concentration pollution measurements and decreases the cost of pollution measurement systems having a wide geographic coverage. In a related embodiment, the invention illustrates a method and system to remotely and automatically calibrate one or more of the low cost sensors disclosed herein as well as other commercially available sensors (such as optical particle counters, photometers etc.) against a reference instrument (such as a beta attenuation monitor) which may or may not be physically located in the same place as the individual sensors. The method may require minimum (or no) user interaction and the calibration period is adjustable periodically.

4 Claims, 8 Drawing Sheets

(56) References Cited

U.S. PATENT DOCUMENTS

| | | | |
|---|---|---|---|
| 8,066,494 B2 | 11/2011 | Kamitani et al. | |
| 8,351,035 B2 | 1/2013 | Goohs et al. | |
| 8,678,787 B2 | 3/2014 | Hirata et al. | |
| 2006/0272393 A1* | 12/2006 | Jenkins | G01N 1/2205 73/31.03 |
| 2014/0347663 A1* | 11/2014 | Rodes | G01N 1/2273 356/338 |

* cited by examiner

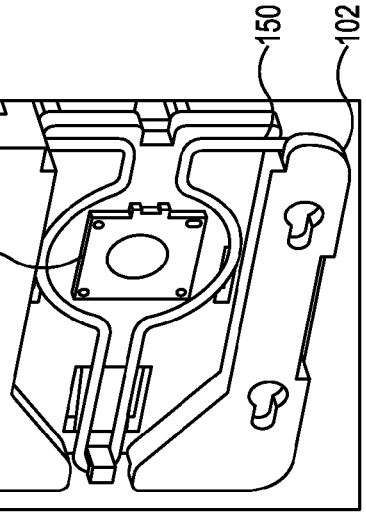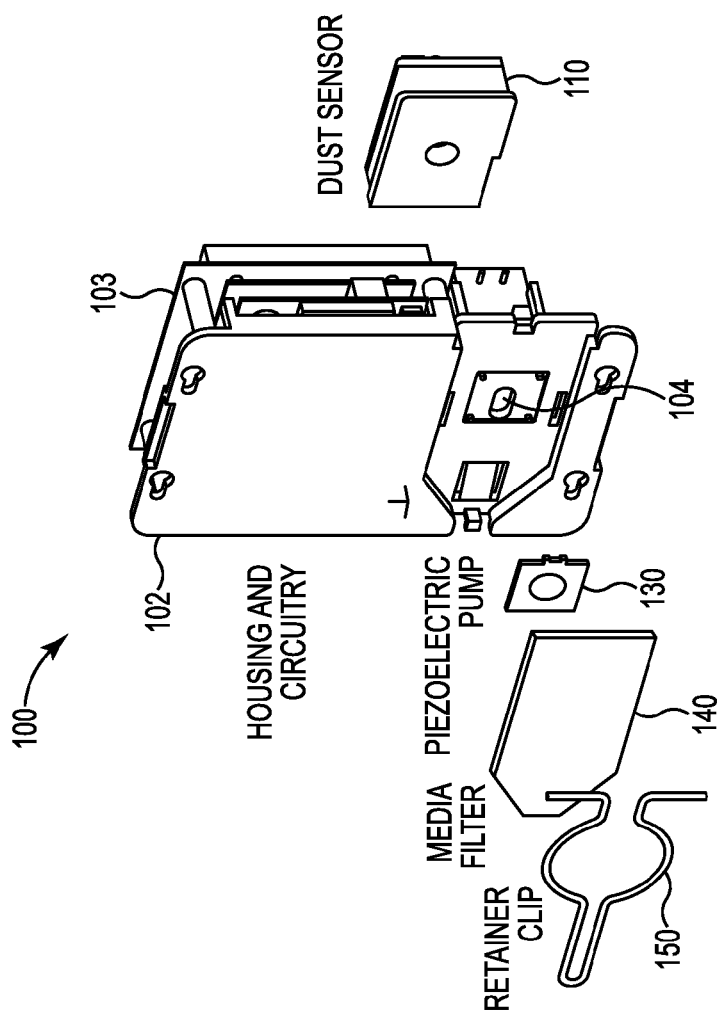

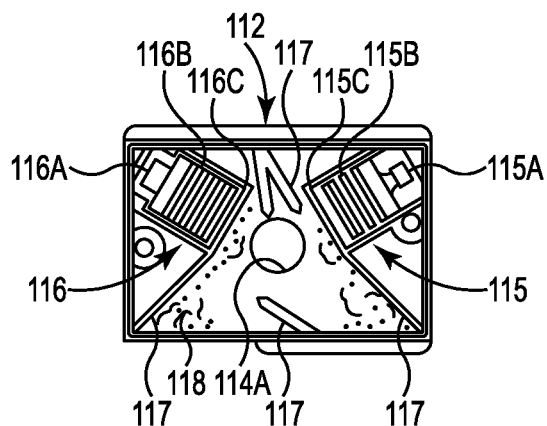
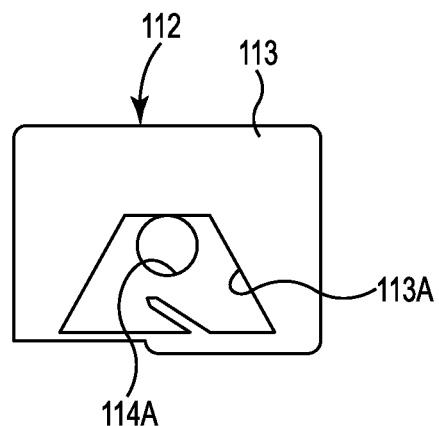
Fig. 3A  Fig. 3B
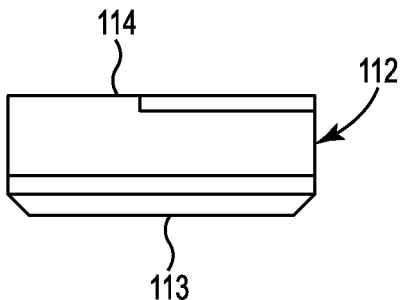
Fig. 3C
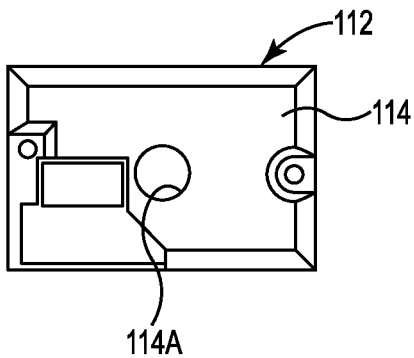
Fig. 3D

SYSTEM AND METHOD OF CONDUCTING PARTICLE MONITORING USING LOW COST PARTICLE SENSORS

CLAIM OF PRIORITY

This application claims priority to and the benefit of U.S. Provisional Patent Application No. 62/086,414, filed Dec. 2, 2014 and titled "SYSTEM AND METHOD OF CONDUCTING PARTICLE MONITORING USING LOW COST PARTICLE SENSORS" which application is incorporated herein by reference in its entirety.

FIELD AND BACKGROUND OF THE INVENTION

The invention generally relates to the detection of particles, and more specifically to the measurement of dust particle concentrations and size distributions.

When inhaled, aerosol particles can deposit on the respiratory track and cause adverse health effects. Hence, industry and government have recognized the importance of measuring and monitoring aerosol concentrations in the environment or workplace so that proper measures can be taken to reduce potential health risks. Pertinent monitoring applications include but are not limited to commercial building or home air quality monitoring, industrial/occupational hygiene surveys, outdoor ambient/site perimeter monitoring for dust control operations, and engine emission studies. Some industrial processes require knowledge of the particulates in the environment, including environments having a sparse population of particles (e.g., semiconductor clean room manufacturing or pharmaceutical drug processing) as well as environments having an extensive presence of particle populations (e.g., dry powder manufacturing processes). In 1987, the United States Environmental Protection Agency (EPA) revised the National Ambient Air Quality Standards (NAAQS) and started to use mass of particles with aerodynamic diameters less than approximately 10 µm (hereinafter "the PM10") as the particulate matter (PM) pollution index. The PM10 is an index of the PM that can enter the thorax and cause or exacerbate lower respiratory tract diseases, such as chronic bronchitis, asthma, pneumonia, lung cancer, and emphysema. It was later determined that PM concentrations in the air, as indexed by the mass of particles with aerodynamic diameters less than approximately 2.5 µm ("PM2.5") was more closely associated with the annual mortality rates than with the coarser PM10. In 1997, in its next revision of the NAAQS, the EPA promulgated regulations on PM2.5.

The American Conference of Governmental Industrial Hygienists (ACGIH) has also established sampling conventions of respiratory, thoracic and inhalable aerosols, defined as particles having aerodynamic diameters of less than 4 µm, 10 µm, and 100 µm respectively. Inhalable particles are those capable of entering through the human nose and/or mouth during breathing. Thoracic particles are the inhaled particles that may penetrate to the lung below the larynx. Respiratory particles are the inhaled particles that may penetrate to the alveolar region of the lung. A discussion of the various sampling conventions are found at National Primary and Secondary Ambient Air Quality Standards, 40 Code of US Federal Regulation, Chapter 1, Part 50 (1997) and Vincent, J. H., Particle Size-Selective Sampling for Particulate Air Contaminants Cincinnati, ACGIH (1999), both of which are hereby incorporated by reference except for explicit definitions contained therein.

While the aforementioned standards and conventions are based on the aerodynamic diameters of particles, it is understood that size segregated mass concentration groupings (e.g., PM1, PM2.5, PM10, respirable, thoracic and inhalable) may be based on the optical particle diameters instead of the aerodynamic diameters for purposes of the instant application. That is, PM2.5 (for example) may approximate particles having an aerodynamic diameter of less than approximately 2.5 µm or particles having an optical diameter of less than approximately 2.5 µm. Particle mass measurements can be achieved in real time using a photometer if the aerosol is primarily a fine aerosol (approximately between 0.1- and 4-µm). The photometer is a device that produces an electrical signal that varies with the intensity of scattered light received from a particle or an ensemble of particles in the interrogation volume region. The photometric signal can be approximately correlated to particle mass. The photometer may also be sensitive to a wide dynamic range of particle concentration. For example, the TSI Model 8520 DUSTTRAK photometer measures a particle mass concentration range of 0.001- to 100-mg/m$^3$ over the particle size range of 0.1- to 10-µm.

Government regulations exist in many countries that require monitoring of various pollution parameters. Instrumentation for measuring these parameters according to regulations tends to be expensive, on the order of $15K-$100K, and the operational costs can be very expensive as well. Due to the cost, there are few instruments in a given geographical area to indicate air quality. Since pollution sources can be localized, there is a great deal of interest in measuring at many points within a geographical area. Sensors for many distributed measurements must be inexpensive but still give a fairly accurate measurement compared to higher precision instruments. There are low-cost techniques for giving an indicative measurement of particulate mass but they are very limited in accuracy. The most common are photometric sensors that measure an ensemble of light scattered from a light source (usually a laser, LED or other source of intense light) and detected by a photodetector (usually a photodiode or other sensitive light detector). The most common low-cost option is an LED light source and photodiode detector. These types of sensors incorporate electronics that convert the signal from scattered light to an electrical signal that can be processed to give a user an indication of particle mass on a display.

In other instances, gravimetric sampling is used which consists of collecting particles, usually over a long period of time such as 24 hours, on a pre-weighed filter. The weight of the filter and particles are then measured. The difference in weight between the filter before and after sampling provides the weight of the particles in a given period of time for a given sampling volume. Some of the advantages of filter sampling include: 1) it is relatively inexpensive to set up and implement and then interpret the data; and 2) the concepts of measurement based on first principles are easier to grasp and share with other interested parties. Other the other hand, gravimetric filtering does have a higher total cost of measurement which includes a great deal of labor cost making it very expensive, trying to measure low particle concentrations can be very difficult since the measurement is a difference in two weight conditions (unused and used filter), poor time resolution, the process is labor intensive and operator error is a possibility, and particles may evaporate before they are weighed.

Photometer sensors tend to require frequent calibration of zero and span due to sensor drift with temperature, humidity or other outside factors. Some disadvantages of various photometers are: (1) only the total mass is measured (no particle size segregated mass information is provided); (2) the photometric signal is dependent on particle properties such as size, shape and refractive index, thus requiring different calibration factors for different aerosols; (3) photometers are typically more sensitive to particles having diameters close to the wavelength of the light source, with a precipitous drop off in signal per unit mass for particles outside of this size range; and (4) photometers can underestimate particulate mass if the sampled aerosol contains particles larger than 4 µm.

One instrument that measures particle size dependent number concentrations in real time is the optical particle counter (OPC). In an OPC, individual particles pass through an interrogation volume that is illuminated by a light beam. The light scattered by each particle is collected on to a detector to generate an electrical pulse. From the pulse height and/or pulse area (i.e. the intensity of the scattered radiation) one can infer the particle size based on prior calibration. Because the size inferred from the OPC depends on the particle optical properties, the inferred parameter is often referred to as the "optical equivalent particle size." Some advantages of the OPC are: (1) particles may be counted with high accuracy for low particle concentrations; (2) favorable signal to noise ratios for particle sizes greater than 1 µm; and (3) low cost. However, the inferred particle optical size may not be the same as the actual or geometric particle size because the determination depends on the particle shape and refractive index assumptions. Additional errors may arise when converting the particle size distribution to a mass concentration if the particle density is incorrectly assumed. Furthermore, OPCs typically underestimate particle concentration when multiple particles are present in the interrogation volume region (a condition often referred to as "coincidence error"). Accordingly, OPCs are typically only used in relatively clean environments. An example is the TSI Model 9306 OPC, which counts 95% of particles at a number concentration of approximately 200 particles/cm$^3$ or mass concentrations less than 1-mg/m$^3$. The counting efficiency of the Model 9306 drops quickly as concentration increases above these limits.

In summary, filter sampling provides first principle mass measurement, but has poor time resolution and it does not provide particle size information. Obtaining size segregated mass concentration measurements may require the procurement and maintenance of multiple instruments. The photometer measures a wide particle concentration range, but it does not provide particle size information and may be relatively insensitive to particles having diameters greater than approximately 4-µm. An instrument and system that can provide size segregated particle mass concentrations information in real time and over a wide range of mass concentrations and a wide geographical area at a competitive cost and simplifies remote calibration of would be a welcome improvement.

SUMMARY OF THE INVENTION

The various embodiments of the invention provide a field calibratable particle sensor solution in a low-cost, very compact form factor. This makes a low-cost sensor more accurate for low-concentration pollution measurements and decreases the cost of pollution measurement systems having a wide geographic coverage.

In a related embodiment, the invention illustrates a method and system to remotely and automatically calibrate one or more of the low cost sensors disclosed herein as well as other commercially available sensors (such as optical particle counters, photometers etc.) against a reference instrument (such as a BAM—beta attenuation monitor) which may or may not be physically located in the same place as the individual sensors. The method may require minimum (or no) user interaction and the calibration period is adjustable periodically (hourly, daily, weekly, etc. . . . ). Optical sensor calibration is used to explain this example embodiment of the invention.

Optical sensors such as optical particle counters and photometers are commonly used in the aerosol field. These sensors measure the light scattered or attenuated by the particles. The light signal depends strongly on the aerosol properties namely refractive indices and morphology. The effect of the refractive indices and morphology can be taken into account by either performing theoretical scattering modeling if aerosol optical properties are known or calibrating the instruments against a measurement reference. If the optical sensors are calibrated against a non-optical reference instrument, then there is an additional benefit in that using this method, optical signals measured by these sensors would automatically be converted to another useful aerosol property of interest. For instance, if the optical sensors are calibrated against a reference mass measurement instrument, instead of showing optical signals, these sensors can then provide aerosol mass information. If the reference instrument is an aerodynamic size measurement instrument, these optical sensors can then be used to measure aerosol aerodynamic size after calibration. Ideally, optical sensors should be re-calibrated every time the composition of the aerosol changes. In practice, however, calibration is usually only done infrequently because the reference instruments are typically only available in the laboratories or at certain fixed locations due to their large size and high cost. Further, the calibration process is typically labor intensive and expensive so it is not practical to perform calibrations frequently in the field. One example embodiment of the invention provides a method and system to calibrate these remotely located sensors easily and without the requirement of having a reference instrument physically located in the same place as the sensor(s).

In one example embodiment, there is provided a sensor assembly for sensing low concentrations of particulate matter that includes a housing having a front and rear portions wherein the rear portion includes an air channel configured to direct a sampled particle aerosol from the rear portion through to the front portion. The assembly further includes a particle sensor device having a front and rear surface and a flow channel therethrough that spans from the rear surface to the front surface, the rear surface of the particle sensor device disposed over the housing air channel such that at least a portion of the sampled particle aerosol flows into the flow channel of the particle sensor device. In addition, a microblower member interposed between the air channel of the housing and the rear surface of the particle sensor device, the microblower adapted to periodically push air through the flow channel of the particle sensor device so as to zero the particle sensor before a subsequent reading; and a filter element is disposed adjacent the microblower and the air channel. In a related embodiment, the sensor assembly forms part of an air quality monitoring system having at least one sensor assembly that may be field calibrated, at least one sensor assembly communicatively coupled to a mobile device, the mobile device in communication with a server adapted to receive a calibration factor, wherein the calibration factor is generated from data received from a reference instrument and from a transfer standard module, one of which is remotely located from the at least one sensor to be calibrated.

In another example embodiment, there is provided a particle sensor assembly calibration system that includes at least one remotely located particle sensor assembly configured to be calibrated in association with at least one reference instrument, wherein the at least one reference instrument is configured to generate a calibration factor. In addition, a mobile device configured to communicate with the at least one reference instrument and with the at least one remotely located particle sensor assembly.

In yet another example embodiment, there is provided a particle sensor assembly calibration system that includes at least one remotely located particle sensor assembly configured to be calibrated in association with at least one reference instrument, wherein the at least one reference instrument is configured to generate a calibration factor. In addition, a control device configured to communicate with the at least one reference instrument and with the at least one remotely located particle sensor assembly.

The novel features of the various embodiments the invention itself, both as to its construction and its method of operation, together with additional advantages thereof, will be best understood from the following description of specific embodiments when read in connection with the accompanying drawings.

BRIEF DESCRIPTION OF THE DRAWINGS

Other important advantages of the invention will be apparent from the following detailed description of the invention taken in connection with the accompanying drawings in which:

FIGS. 1A-1B are exploded and inset views, respectively, of a low cost particle sensor assembly in accordance with an example embodiment of the invention;

FIGS. 3A-3D are views of a dust sensor device used in the particle sensor assembly in accordance with an example embodiment of the invention;

DETAILED DESCRIPTION OF THE INVENTION

Figure 2A:
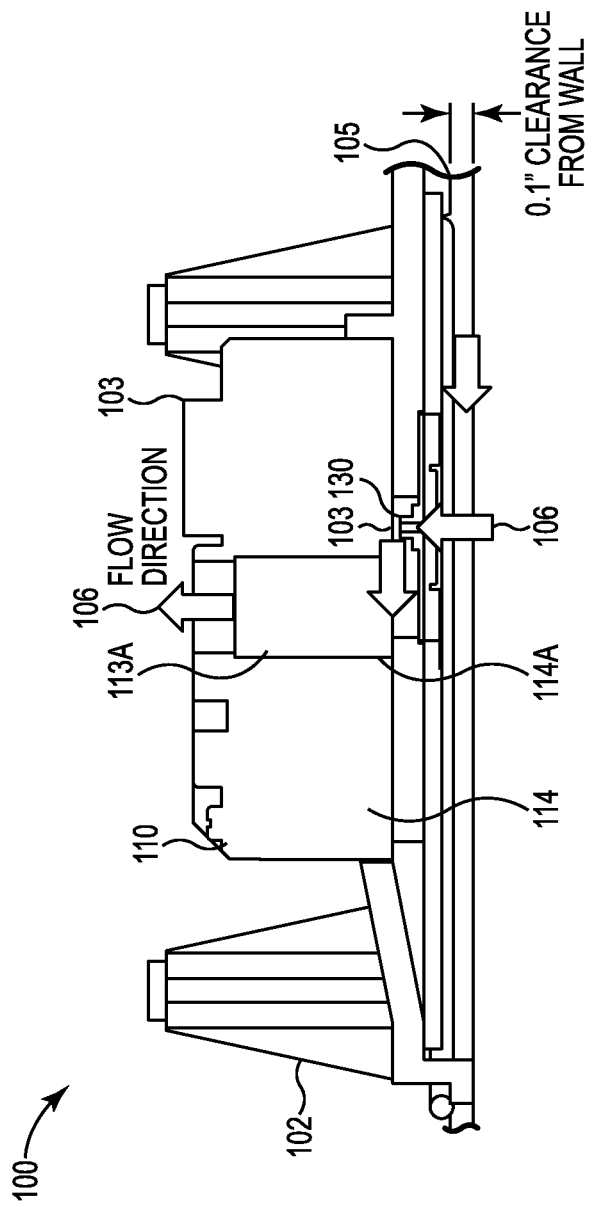
FIGS. 2A-2B are side cutaway and 3-D views of the particle sensor assembly as taught herein and the direction of flow of the aerosol sample being taken in accordance with an example embodiment of the invention.
Figure 2B:
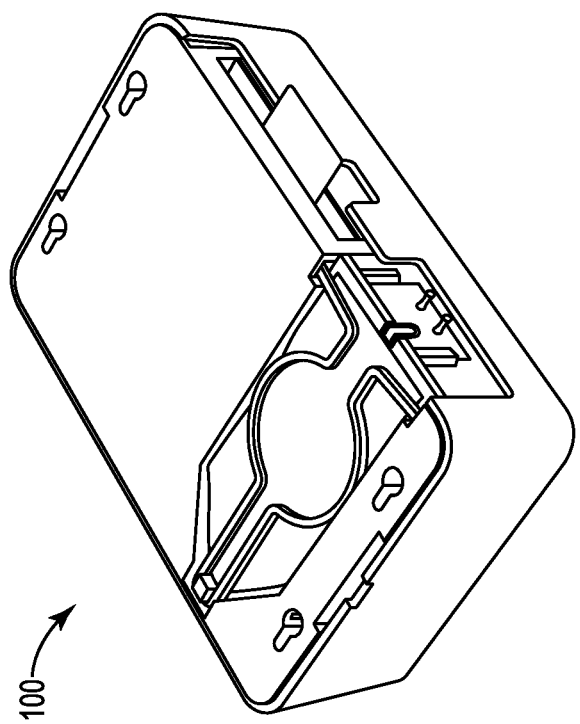

Following are more detailed descriptions of various related concepts related to, and embodiments of, methods and apparatus according to the present disclosure. It should be appreciated that various aspects of the subject matter introduced above and discussed in greater detail below may be implemented in any of numerous ways, as the subject matter is not limited to any particular manner of implementation. Examples of specific implementations and applications are provided primarily for illustrative purposes.

In one example embodiment, there is disclosed an inexpensive and very compact device that addresses the requirement of frequent zero calibration of a low-cost sensor. The low-cost particle sensor incorporates a unique and compact piezoelectric microblower and filter material to periodically pass filtered air through a photometric sensor to provide more accurate low-concentration measurements. In this example embodiment, the piezoelectric microblower has an advantage over other air movers in that it can provide enough pressure head across a filter to drive a significant flow (about 1 LPM) to provide clean air to a dust or particle sensor component in a very small package. This particle sensor assembly has application in indoor and outdoor air measurement systems of PM 2.5 or other air pollution measurements. The specific design incorporates several design features that adapt a microblower or micropump of this type to the application. In a related embodiment, such a low cost particle sensor facilitates implementation of an overall particle monitoring system that spans over a large geographical area due to improved system cost for a user.

Referring now to the figures, and in particular FIGS. 1A-3, there is illustrated in FIGS. 1A-1B exploded and inset views, respectively, of a low cost particle sensor assembly 100 in accordance with an example embodiment of the invention. In this example embodiment, particle sensor assembly 100 includes a housing 102 that supports a circuit board 103, an aperture 104 for sample air flow, a dust sensor 110, a piezoelectric microblower 130 adapted to fit into aperture 104, a filter media 140 for the rear of microblower 130 and a retainer clip 150 that holds all of the components together. Inset view of FIG. 1B illustrates the various components above all assembled. FIG. 2B illustrates a 3-D view of particle sensor assembly 100 fully assembled. In this embodiment, microblower 130 is as described in detail in U.S. Pat. No. 8,678,787, which is incorporated by reference herein in its entirety. In a related embodiment, blower 130 is configured from other designs and is configurable to be a micro pump, as described in U.S. Pat. No. 8,066,494, which is incorporated by reference herein in its entirety.

Figure 4:
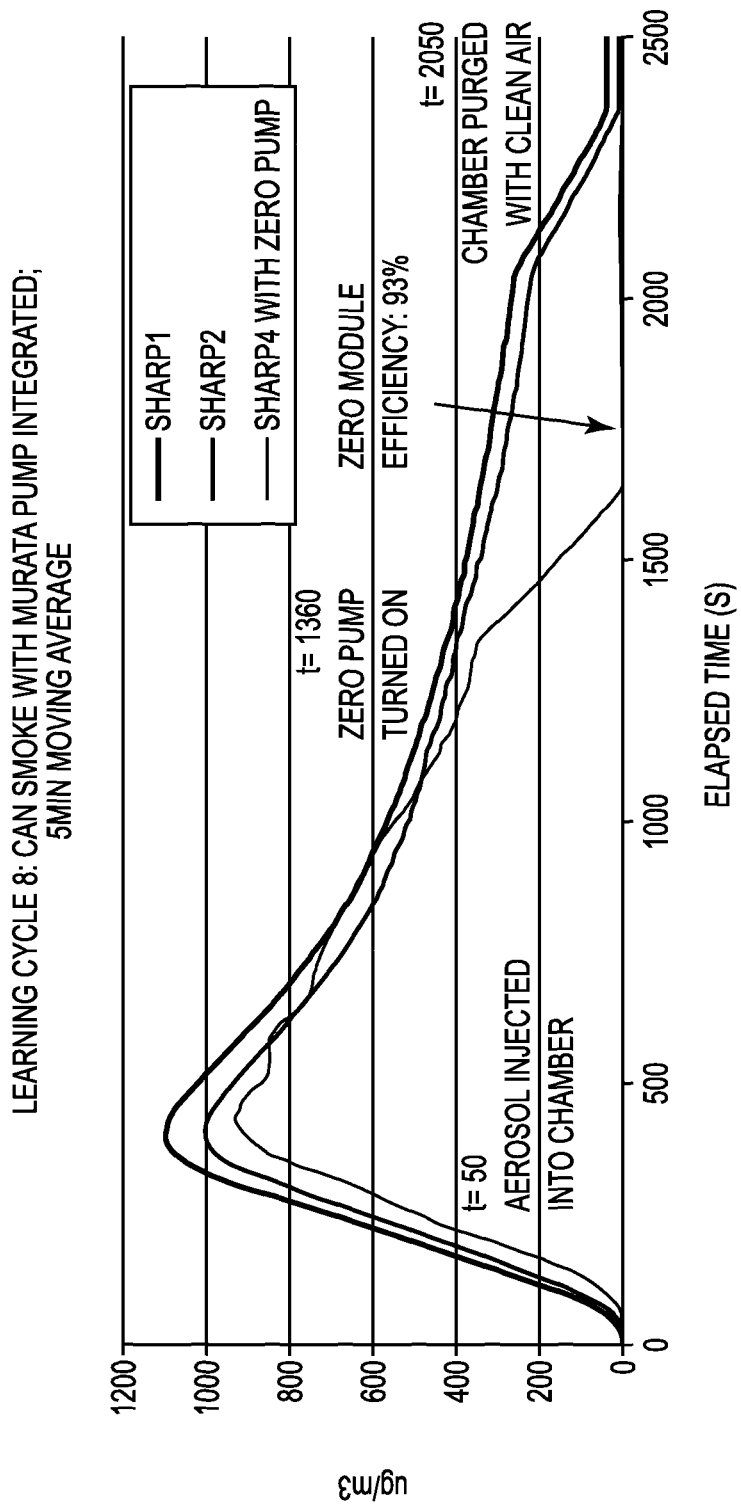
FIG. 4 is a graph illustrating the particle sensor assembly performance as taught herein in various conditions.

Referring now to FIG. 2A, there is shown a cutaway side view of particle sensor assembly 100 as taught herein illustrating a flow channel 105 in housing 102 in which sampled air travels in the direction of flow 106 and moves through microblower 130 and cylindrical channel 114A of dust sensor 110. During operation, air to be sampled flows through flow channel 105 along a wall of housing 102 and then is directed through cylindrical channel 114A in which a light is directed perpendicular to the flow through channel 114A. In this example embodiment, the filter element is on the outside of the housing such that the particle laden aerosol flow goes through the filter, then through the microblower and then through the dust sensor. In this example embodiment, blower or pump 130 uses a piezoelectric crystal that has a very compact size and is easily driven by electronics. Piezoelectric microblower 130 provides significant flow (about 1 lpm) to provide clean air to dust or particle sensor 110 in a very small package. The design allows for easy installation and replacement of filter media 140. It also diffuses the high-velocity output of the pump so it can clean out a larger sensor space in a short time. The pump routes sample air flow without the use of tubing or O-rings. FIG. 4 is a graph illustrating performance of the particle sensor assembly 100 as taught herein in various conditions, where the detection chamber is purged with clean air (Sharp 4 with Zero pump) to improve the accuracy of the dust sensor at very low concentrations.

The following data shows results of an experiment for evaluating a micro-blower C having a diaphragm including an annular piezoelectric element. First, there was prepared a diaphragm formed by attaching a piezoelectric element to a brass plate 0.1 mm in thickness. The piezoelectric element was composed of a single annular PZT plate 0.2 mm in thickness, 18 mm in outside diameter, and 5 mm in inside diameter. Next, there were prepared a separator composed of a brass plate; and a top plate, a flow path plate, a blower frame, and a bottom plate composed of SUS plates. A second opening 1.0 mm in diameter was provided at the center of the top plate. A first opening 0.8 mm in diameter was provided at the center of the separator. A center space 6 mm in diameter and 0.5 mm in height was provided at the center of the flow path plate. Next, the above-described components were stacked in the following order: the bottom plate, diaphragm, blower frame, separator, flow path plate, and top plate. They were bonded together to form a blower body measuring 20 mm long by 20 mm wide by 4.0 mm high. The blower chamber of the blower body was designed to be 0.05 mm in height and 18 mm in diameter.

When a sine wave voltage of 25.2-kHz frequency and 60 Vp-p was applied to drive the micro-blower C having the above-described structure, a flow rate of 700 ml/min at 100 Pa and a maximum developed pressure of 0.7 kPa were obtained. Although this is an example where the micro-blower C was driven in the third-order mode, it is also possible to drive the micro-blower C in the first-order mode.

Referring now to FIGS. 3A-3D, there are a sectional, front, bottom, and rear views, respectively, of optoelectronic dust sensor 110 used in sensor assembly 100. An opening 113a is formed at front panel 113 of main body housing 112, and flow channel or passage hole 114a is formed at back panel 114 of main body housing 112, with the flow channel or dust passage route permitting passage of dust and/or smoke or smog being provided between passage hole 114a of back panel 114 and opening 113a of front panel 113. Passage hole 114a is for introducing dust and/or smoke to the dust passage route. Opening 113a, being for discharging dust and/or smoke from the dust passage route, is sufficiently larger than passage hole 114a. In this example embodiment, microblower 130 is located at or near hole 114a of sensor 110 so as to push air through sensor 110 to clean and zero out the device by periodically activating the microblower. The microblower may be activated for a few minutes per hour or per week for this purpose. In one example embodiment the flow, although temporary, is a continuous, generally pulse-free air flow, and it is continuously on for a period of 2-5 minutes in one example embodiment. Further, it can be periodic, such as once per minute or once per week.

Furthermore, a light-emitting unit 115 and a light-receiving unit 116 are respectively arranged so as to be directed toward the dust or particle passage route. In this example embodiment, a plurality of optical baffles 117 are arranged in distributed fashion as appropriate, preventing light from light-emitting unit 115 from being directly incident on light-receiving unit 116 and forming optical isolation region (s) 118. In this example embodiment, light-emitting unit 115 is equipped with light-emitting element 115a, lens 115b, and slit 115c; light from light-emitting element 115a being collimated by lens 115b. The cross-section of the collimated light beam is narrowed and/or shaped by slit 115c, and this thereafter exits therefrom such that it is directed at the dust passage route. Light-receiving unit 116 is equipped with light-receiving element 116a, lens 116b, and slit 116c; with light from the dust passage route being condensed onto light-receiving element 116a by way of slit 116c and lens 116b.

In this example embodiment, lens 115b and slit 115c of light-emitting unit 15 cause the light from light-emitting element 115a to be concentrated in which light from light-emitting element 115a could be dispersed and reflected within main body housing 112, thereby causing unwanted light to be incident on light-receiving unit 116. Furthermore, lens 116b and slit 116c of light-receiving unit 116 cause light which is reflected by dust and/or smoke in the dust passage route to be received at light-receiving element 116a, thereby preventing situations in which unwanted light reflected within main body housing 112 is received at light-receiving element 116a. In the event that there is no dust or smoke passing through the dust passage route, then light from light-emitting unit 115 will pass through the dust passage route and reach optical isolation region 18, hence at this optoelectronic dust sensor 110 will sense that the amount of light received at light-receiving unit 116 will be extremely small.

Conversely, in the event that there is dust and/or smoke or smog passing through the dust passage route, because a portion of the light from light-emitting unit 115 will be reflected by the dust and/or smoke in the dust passage route and will be incident on light-receiving unit 116, the amount of light received at light-receiving unit 116 will increase. Accordingly, presence and/or absence of dust and/or smoke passing through the dust passage route may be detected based on variation in received-light output at light-receiving element 116a of light-receiving unit 116. In addition, the concentration of dust and/or smoke passing through the dust passage route may be detected based on the received-light output level at light-receiving element 116a. A further description of the operation and the electronic circuits forming the optoelectronic sensor 110 is described in U.S. Pat. No. 7,038,189, which is incorporated herein by reference in its entirety.

Figure 5:
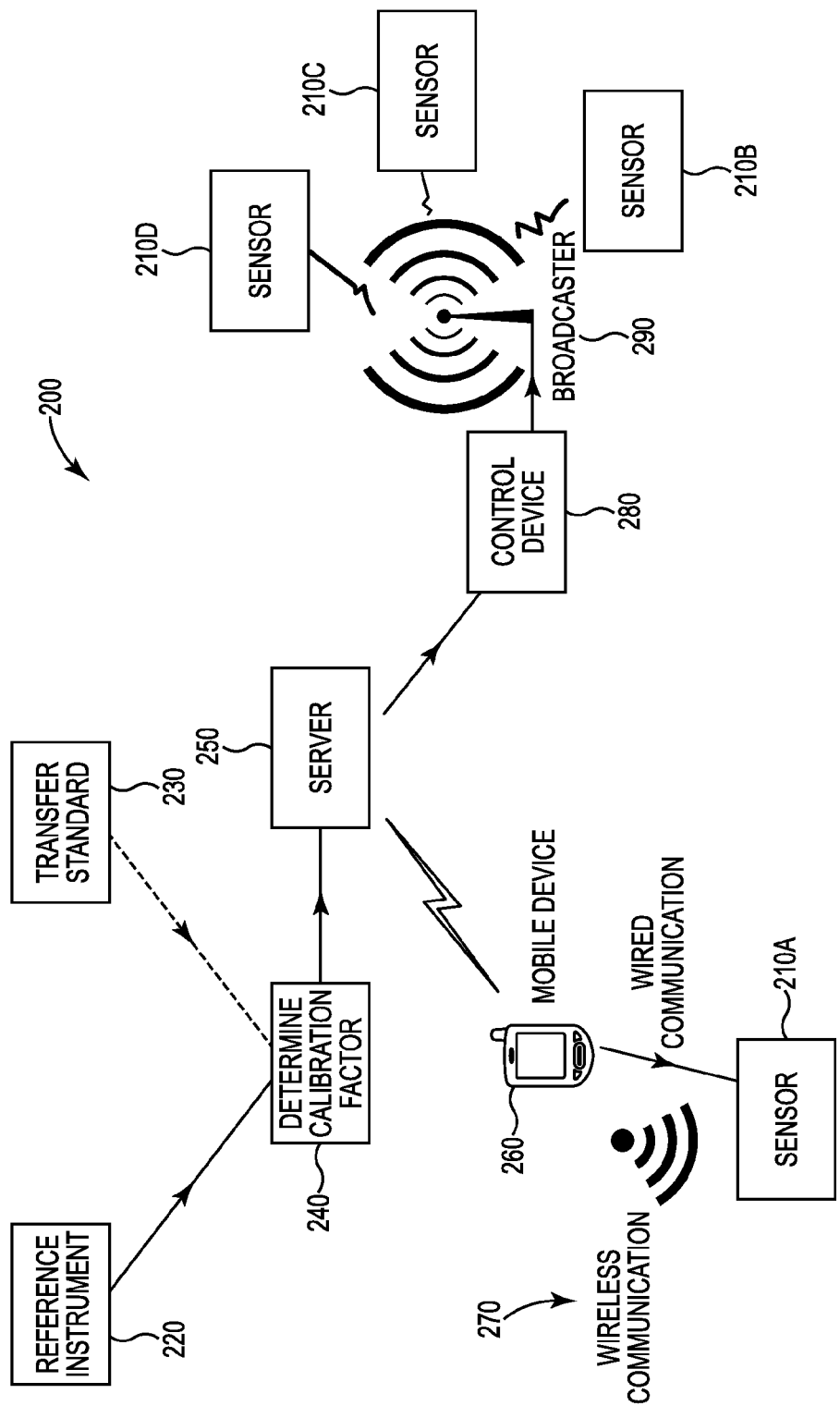
FIG. 5 is a top level system diagram of particle sensors that are calibrated remotely in accordance with an example embodiment of the invention.
Figure 6:
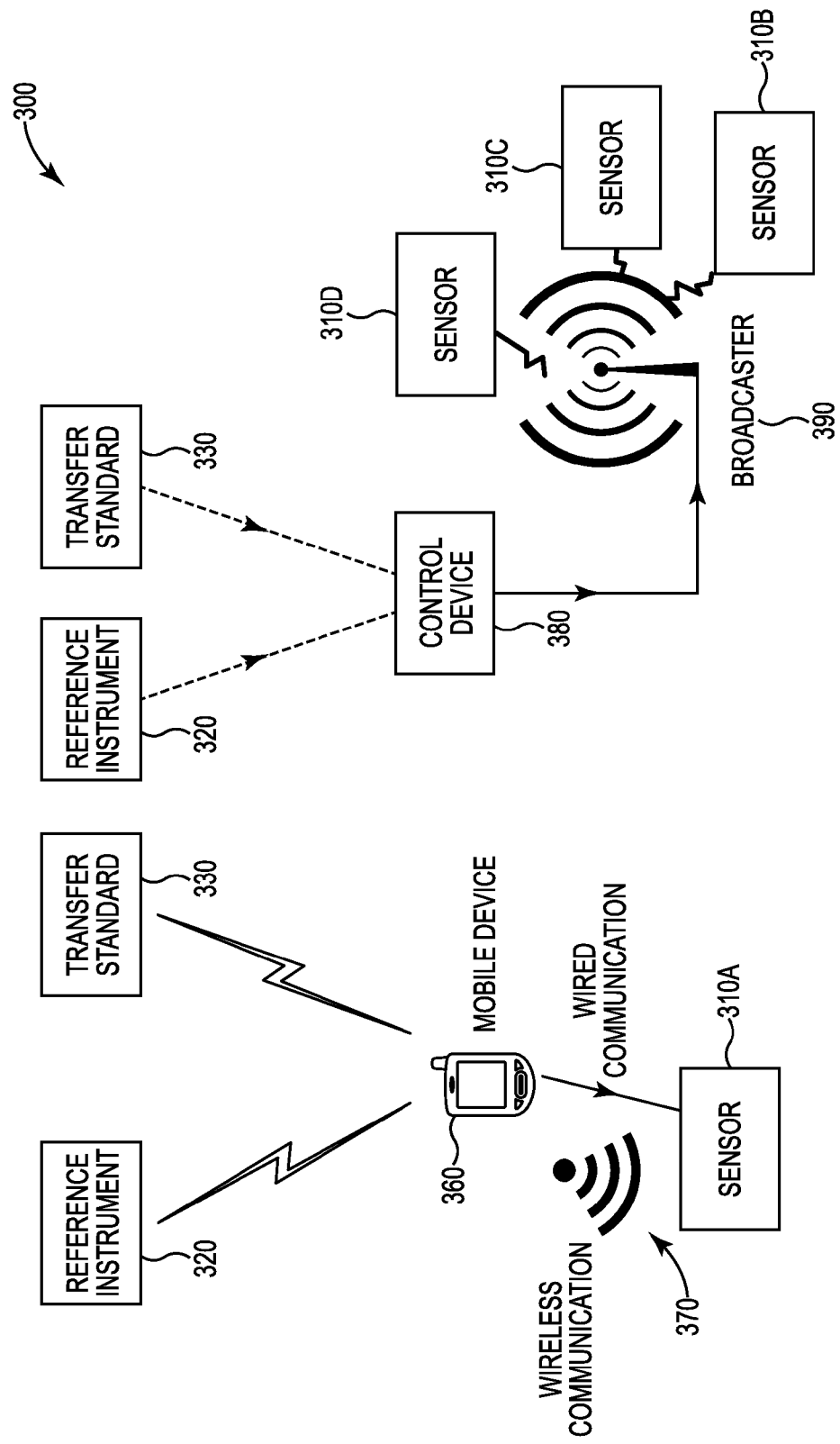
FIG. 6 illustrates a system and method of calibrating particle sensors using an internet server in accordance with an example embodiment of the invention.
Figure 7:
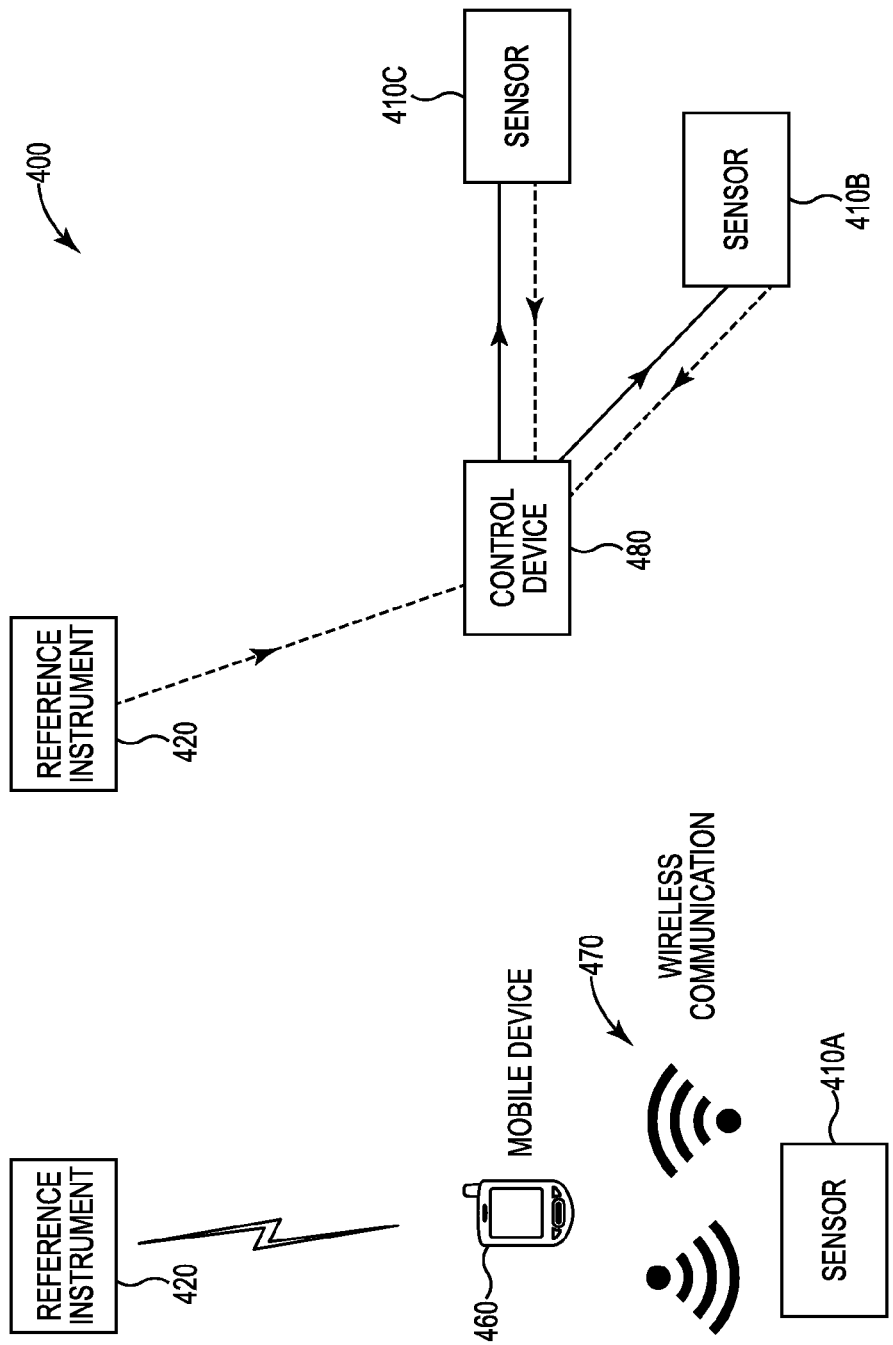
FIG. 7 illustrates a system and method of calibrating particle sensors using an internet server and a transfer standard in accordance with an example embodiment of the invention

Referring now to FIGS. 5-7, and in particular FIG. 5, there is illustrated a high level view of system and method 200 for remotely calibrating one or more particle sensors with one or more reference instruments that are not necessarily co-located with each other in accordance with an example embodiment of the invention. In particular, system 200 includes a plurality of particle sensors 210A-210D that are deployed in the field along with one or more reference instrument(s) 220 and a transfer standard module 230 that is used to facilitate the remote sensor calibration process. To ensure good calibration, transfer standard module 230 is preferred to be (but not necessarily limited to): (1) the same type of particle sensor which is under calibration or (2) a sensor that provides good correlation to the particle sensors under calibration. The readings of reference instrument 220 and transfer standard module 230 are first made available on the Internet or some other communications network. This can be done in a number of ways including uploading the data to a web site, sending the data via a short message (for instance, social media service Twitter) or via a text. A software module or firmware then downloads to reference instrument 220 and transfer standard module 230 readings or data from the Internet to a calibration factor module 240. A calculation or processing of such data/readings is then performed at a calibration factor module 240 to determine the calibration factor to be used on the remote particle sensors. Since different calibration factors may be necessary at different locations or cities, the calibration factor specified to a certain location/city could be determined by using reference instrument 220 and transfer standard module 230 stationed in that particular location/city. Then a lookup table is generated and it consists of information about calibration factors at various locations or cities. This lookup table is then uploaded to a server 250. The content of this lookup table may refresh at certain periods such as hourly, daily, weekly, etc.

Once the lookup table is generated and uploaded to server 250, there are two ways to calibrate the sensors in the field. One way is to use a mobile device 260 to download the lookup table from the internet and then transfer or transmit the calibration factor to particle sensor 210A based on the location information stored in the sensor. The communication between mobile device 260 and sensor 210A is either wired or wireless communication 270. If the calibration factor is not available at this location, users are able to input a custom calibration factor, use a value previously stored in the particle sensor, or use an interpolated value based on the location of the particle sensor to be calibrated and its nearest reference instruments and transfer standards. The previous stored value could also be the factory-calibrated value. Since the signal from mobile device 260 may have very limited transmission range, it is possible only one particle sensor could be calibrated at a time.

In a related embodiment, in order to calibrate multiple particle sensors at a time, a control device 280 and a broadcaster module 290 are used and integrated into the calibration system. Control device 280 could be a computer or server while broadcaster module 290 could be a Wi-Fi router, Bluetooth device or a radio frequency broadcaster. Control device 280 downloads the lookup table from the internet or server 250, determines the calibration factor based on the physical location of the particle sensor, and then sends the calibration factor to all of the particle sensors 210B-210D via the broadcaster. The frequency of calibration of the sensors is configurable by control device 280.

Referring now to FIG. 6 there is illustrated a system 300 and method of calibrating particle sensors 310A-310D without using an internet server in accordance with an example embodiment of the invention. In this embodiment, the calibration factor is determined directly by mobile device 360 or control device 380 (as shown in FIG. 6). Hence, an internet server which maintains the lookup table as in the previous embodiment is not required here. Similar to the previous embodiment, the calibration factor is transmitted to the sensors 310A-310D either by one-sensor-at-a-time or multiple-sensors-at-a-time methods. In the various embodiments disclosed herein, the reference instrument includes a beta attenuation monitor (BAM), which is commercially available from such manufacturers as Thermo Fisher Scientific, Inc. of Minneapolis, Minn., or includes one or more low cost sensors such as described herein in FIGS. 1-3. In this example embodiment, a calibration factor is determined or generated by comparing the low cost sensor reading with other low cost sensors in the same general area.

Referring now to FIG. 7, there is illustrated a system 400 and method of calibrating particle sensors 410A-410C that does not use an internal server and a transfer standard in accordance with an example embodiment of the invention. In this embodiment of the invention, a calibration factor is determined or generated without the transfer standard by comparing the data from the reference instrument 420 and one particle sensor, such as sensor 410A. Unlike the previous embodiments, this calibration scheme or configuration uses two-way communication 470 to accomplish the remote sensor calibration against a standard or reference instrument. When calibrating multiple sensors, control device 480 communicates with reference instrument 420 and with one or more sensors 410B-410C to arrive at a calibration factor and ultimately calibrating the remote particle sensors.

One application of the remote calibrating method and systems described herein are for calibrating aerosol optical sensors deployed in the field. Optical sensors such as optical particle counters, photometers are commonly used in the aerosol monitoring field. These sensors either measure the light scattered or attenuated by the particles. The light signal depends strongly on the aerosol properties namely refractive indices and morphology. The effect of the refractive indices and morphology can be taken into account by either performing theoretical scattering modeling if aerosol optical properties are known or calibrating the instruments against a measurement reference.

If the optical sensors are calibrated against a non-optical reference instrument, there is an additional benefit that optical signals measured by these sensors would automatically be converted to another aerosol property of interest. For instance, if the optical sensors are calibrated against a reference mass measurement instrument, instead of showing optical signals, these sensors can provide aerosol mass information. If the reference instrument is an aerodynamic size measurement instrument, these optical sensors can then be used to measure aerosol aerodynamic size after calibration. Ideally, optical sensors should be re-calibrated every time the composition of the aerosol changes. In practice, however, calibration is usually only done infrequently because: 1) the reference instruments are typically only available in the laboratories or certain fixed locations due to their large size and high cost, or 2) the calibration process is typically labor intensive and expensive hence it is not practical to perform calibrations frequently in the field. The teachings herein provide a method to calibrate these optical sensors easily and without the requirement to have a reference instrument located in the same place. In this example, optical sensors are calibrated to monitor mass of particulate matter (PM) less than 2.5 µm. This mass value is commonly referred to as PM2.5 and it is widely used as an air quality indicator.

The reference instrument in this example embodiment is a beta attenuation monitoring (BAM) instrument. The BAM determines the mass of particulate matters by comparing the beta radiation attenuation before and after the sample is collected on a filter or thin film. The BAM is commonly used by United States Environmental Protection Agency (EPA) to monitor PM2.5 at various monitoring sites. The technique is widely used in other countries as well. The mass information collected by the BAM devices is usually available to the public on the air monitoring agencies web sites. Some monitoring sites even send the information out hourly using the social media service Twitter. The transfer standard module used in this example embodiment is an optical particle counter or photometer located in a weatherproof enclosure to protect it from the elements. Several of these transfer standard modules could be deployed in big cities where BAM information is available and the data collected by these transfer standard modules is sent to a cloud server. By comparing the data/information from the BAMs and transfer standard modules, calibration factors at various locations/cities can be generated and a lookup table is generated and uploaded to a web server or other network storage location. By using a mobile device, the lookup table can be pulled from the server and the appropriate calibration factor could be transmitted to one or more particulate matter sensors located indoors or outdoors. Using the methods described herein, the various particulate matter sensors in a specified city could be calibrated daily against a reference instrument (in this case a BAM or a low cost sensor as described herein) located somewhere in the city. The daily calibration ensures these sensors take into account the type of aerosol present in that city/region at that time, and thus provide a useful and credible reading.

The following patents and publications are incorporated by reference in their entireties: U.S. Pat. Nos. 5,121,988; 7,111,496 (BAM devices); U.S. Pat. Nos. 7,932,490; 8,009,290; and 8,351,035 (sensor calibration).

The foregoing specific embodiments of the present invention as set forth in the specification herein are for illustrative purposes only. Various deviations and modifications may be made within the spirit and scope of the invention without departing from the main theme thereof.

What is claimed is:

1. A sensor assembly for sensing low concentrations of particulate matter comprising:
   a housing having a front and rear portions wherein the rear portion includes an air channel configured to direct a sampled particle aerosol from the rear portion through to the front portion;
   a particle sensor device having a front and rear surface and a flow channel therethrough that spans from the rear surface to the front surface, the rear surface of the particle sensor device disposed over the housing air channel such that at least a portion of the sampled particle aerosol flows into the flow channel of the particle sensor device;
   a microblower member interposed between the air channel of the housing and the rear surface of the particle sensor device, the microblower periodically pushing air through the flow channel of the particle sensor device to clean and zero calibrate the particle sensor before a subsequent reading; and
   a filter element is disposed adjacent the microblower and the air channel of the housing, the filter element configured to filter the particulates from the air flow temporarily generated by the microblower.

2. The sensor assembly of claim 1 further including a retainer clip adapted to engage a portion of the housing and retain the filter element and the microblower member in the housing.

3. The sensor assembly of claim 1 wherein the microblower member is a micropump.

4. The sensor assembly of claim 1 forming part of an air quality monitoring system, the air quality monitoring system having the sensor assembly that is field calibrated and that is communicatively coupled to a mobile device, the mobile device in communication with a server adapted to receive a calibration factor, wherein the calibration factor is generated from data received from a reference instrument and from a transfer standard module, one of which is remotely located from the sensor assembly to be calibrated.

* * * * *